US008452065B2

(12) United States Patent
Azar et al.

(10) Patent No.: US 8,452,065 B2
(45) Date of Patent: May 28, 2013

(54) SYSTEM FOR DETECTING MALIGNANT LYMPH NODES USING AN MR IMAGING DEVICE

(76) Inventors: Fred S. Azar, Ramsey, NJ (US); Mukesh G. Harisinghani, Lexington, MA (US); Christian P. Schultz, Beverly, MA (US); Ravi Teja Seethamraju, Malden, MA (US)

(*) Notice: Subject to any disclaimer, the term of this patent is extended or adjusted under 35 U.S.C. 154(b) by 566 days.

(21) Appl. No.: 12/717,356

(22) Filed: Mar. 4, 2010

(65) Prior Publication Data

US 2010/0232667 A1  Sep. 16, 2010

Related U.S. Application Data

(60) Provisional application No. 61/159,209, filed on Mar. 11, 2009.

(51) Int. Cl.
*G06K 9/00* (2006.01)

(52) U.S. Cl.
USPC .......................................................... 382/131

(58) Field of Classification Search
CPC ...................................................... G06T 7/0012
USPC ........................................................ 382/131
See application file for complete search history.

(56) References Cited

U.S. PATENT DOCUMENTS 6,473,634 B1 * 10/2002 Barni ............................. 600/425
8,195,275 B2 * 6/2012 Zwick et al. ................... 600/420

OTHER PUBLICATIONS

Takahara et al., "Diffusion Weighted Whole Body Imaging with Background Body Signal Suppression (DWIBS) Technical Improvement Using Free Breathing, STIR and High Resolution 3D Display," Radiation Medicine, vol. 22, No. 4, pp. 275-282, 2004.
Harisinghani et al., "Noninvasive Detection of Clinically Occult Lymph-Node Metastases in Prostate Cancer", NEJM, vol. 348, No. 25, pp. 2491-2499, Jun. 19, 2003.
Viola et al., "Alignment by Maximization of Mutual Information", International Journal of Computer Vision, vol. 24, No. 2, pp. 137-154, 1997.
Chefd'Hotel et al., "Flows of Diffeomorphisms for Multimodal Image Registration", ISBI, 2002, INRIA Sophia-Antipolis, France.
Seethamrayu et al., "High Resolution Non-contrast Lymphangiography of the Head and Neck at 3Tesla", ISMRM, 2008.
Mugler et al., "T2-Weighted 3D Spin-Echo Train Imaging of the Brain at 3 Tesla: Reduced Power Deposition Using Low Flip-Angle Refocusing RF Pulses", Proc. Intl. Soc. Mag. Reson. Med, vol. 9, p. 438, 2001.
Topf et al., "Measuring Quantitative Regional Lung Ventilation by Alveolar Ventilation Imaging (AVI)—Phantom Data and Results of a Reasibility Study in 50 Patients", Proc. Intl. Soc. Mag. Reson. Med., vol. 11, p. 671, 2004.

(Continued)

*Primary Examiner* — Michelle Le
(74) *Attorney, Agent, or Firm* — Alexander J Burke (57) ABSTRACT

A system detects malignant lymph nodes using an MR imaging device, for, in the absence of a contrast agent, acquiring in a patient anatomical volume of interest including lymph nodes, (a) a first image using a variable flip angle, lymph node enhanced contrast, MR image acquisition process, (b) a second image using a susceptibility weighting imaging acquisition process and (c) a third image using a diffusion weighting imaging acquisition process. In the presence of a contrast agent absorbed by benign lymph nodes, MR imaging device acquires in the patient anatomical volume of interest, (d) a fourth image using a susceptibility weighting imaging acquisition process. A display processor processes data representing the first, second, third and fourth images for display of malignant and benign lymph nodes on a reproduction device.

23 Claims, 8 Drawing Sheets

OTHER PUBLICATIONS

Haacke et al., "Susceptibility Weighted Imaging (SWI)", Magnetic Resonance in Medicine, vol. 52, pp. 612-618, 2004.

Park et al., "Optimized T1-Weighted Contrast for Single-Slab 3D Turbo Spin-Echo Imaging With Long Echo Trains: Application to Whole-Brain Imaging", Magnetic Resonance in Medicing, vol. 58. pp. 982-992, 2007.

Harisinghani et al., "Sensitive, Noninvasive Detection of Lymph Node Metastases", PLOS Medicine, vol. 1, Issue 3, Dec. 2004.

* cited by examiner

Different diffusion weighted images co-registered with the SPACE image to show the
localized lymph node (The lymph node is seen in the white oval)

SYSTEM FOR DETECTING MALIGNANT LYMPH NODES USING AN MR IMAGING DEVICE

This is a non-provisional application of provisional application Ser. No. 61/159,209 filed 11 Mar. 2009, by R. T. Seethamraju et al.

FIELD OF THE INVENTION

This invention concerns a system for detecting malignant lymph nodes by adaptively processing images acquired by an MR imaging device that are differently MR weighted, for example, to provide resultant image data.

BACKGROUND OF THE INVENTION

The development of lymph node targeted magnetic nano-materials has significantly enhanced the diagnostic accuracies of Magnetic Resonance imaging (MRI) for nodal staging in cancer. Especially the accuracy of detection in non-enlarged (occult) lymph nodes where the foci of nodal metastases are less than 5 mm. However, comprehensive imaging detection of possible nodal metastasis is desirable in order to maximize therapy but represents a problem for known imaging staging systems. A system according to invention principles provides high resolution 3D (three dimensional) MRI combined with increased detection accuracy for improved detection of potential nodal metastasis.

SUMMARY OF THE INVENTION

A system detects malignant lymph nodes using an MR imaging device, for, in the absence of a contrast agent, acquiring in a patient anatomical volume of interest including lymph nodes, (a) a first image using a T2 weighted variable flip angle turbo or fast spin echo image acquisition process that is optimized to enhance lymph nodes, (b) a second image using a susceptibility (T2*) weighted imaging acquisition process and (c) a third image using a diffusion weighted imaging acquisition process. In the presence of a contrast agent (e.g., a nano-material based contrast agent) absorbed by benign lymph nodes, MR imaging device acquires in the patient anatomical volume of interest including lymph nodes, (d) a fourth image using a susceptibility (T2*) weighted imaging acquisition process. A display processor processes data representing the first, second, third and fourth images for display on a reproduction device.

DETAILED DESCRIPTION OF THE INVENTION

A system detects malignant lymph nodes using an MR imaging device to acquire different types of MR weighted images using corresponding different pulse sequences. The system processes data representing the different types of image to provide image representative data enhancing malignant lymph nodes, for example, for display on a reproduction device. The system in one embodiment automatically identifies the enhanced malignant lymph nodes.

As used herein:

T1 Imaging: T1 is a characteristic time constant that describes the decay of longitudinal magnetization due to spin-lattice relaxation in the human body in MRI.

T2 Imaging: T2 is a characteristic time constant that describes the decay of transverse magnetization due to the spin-spin relaxation in the human body in MRI.

T2* Imaging: (T2*) is the characteristic time constant that describes the decay of transverse magnetization, taking into account the inhomogeneity in static magnetic fields and the spin-spin relaxation in the human body. This results in a rapid loss of phase coherence in an MRI signal.

DWI: DWI comprises diffusion weighted imaging. In this method of imaging, diffusion gradients are applied prior to acquisition of MR signals. The diffusion gradients enable acquisition of an MR signal that is directly related to the diffusibility of water molecules in the tissue.

Susceptibility Weighted Image (SWI): An image that is T2* weighted is designated as being in the class of SWI. Imaging methods may phase modulate magnitude images to enhance images acquired using an external or endogenous contrast agent (SWI—(Susceptibility weighted imaging), Siemens® and SWAN—(T2 Star Weighted Angiography), GE®).

SPACE: SPACE an acronym for Sampling Perfection with Application optimized Contrast using different angle Evolutions comprises a 3D Turbo (FAST) Spin Echo acquisition with a variable flip angle non-selective pulse train for refocusing [2]. This sequence is advantageous for T2 weighted image acquisition, though T1 and proton density weightings may also be employed. A similar sequence is termed Cube/Xeta (e.g., GE®) and VISTA (e.g., Philips®) in other proprietary terminology.

Lymph node: A lymph node is a component of the lymphatic system. A lymph node acts as filter, with an internal honeycomb of connective tissue filled with lymphocytes that collect and destroy bacteria and viruses. When the body is fighting an infection, these lymphocytes multiply rapidly and produce a characteristic swelling of the lymph nodes. Humans have approximately 500-600 lymph nodes. Clusters of lymph nodes are found in the underarms, groin, neck, chest, and abdomen. Lymph nodes are bean-shaped and range in size from a few millimeters to about 1-2 cm in their normal state. They may become enlarged due to a tumor or infection.

USPIO: USPIO stands for Ultra Small Super paramagnetic Iron Oxide nano-particles. USPIOs are a new class of MR contrast agents that are Lymphotropic nano-particles (LNP) which have paved the way for MR in imaging lymph node metastasis. This highly sensitive and specific method has been used on patients with cancers of the prostate, bladder, kidney and breast to identify metastases as small as 1 mm in lymph nodes that have become cancerous. LNPs target macrophages (a type of white blood cells), which are found in abundance in the lymph nodes. The macrophages consider the LNPs as intruders and consume them; a process called phagocytosis. On phagocytosis, the lymph nodes appear dark on T2* weighted images because iron is a highly susceptible metal. Macrophages are absent in lymph nodes that have metastasis in them and hence the LNPs are not collected in these nodes. Due to lack of Iron in these nodes, they appear bright on T2*, hence normal lymph nodes can be distinguished from those that are cancerous.

Fusion: Fusion is a process by which two images from different imaging sequences of the same patient are co-registered and overlaid on each other with different color scales to depict areas of mutual concurrence or lack of it.

Figure 1:
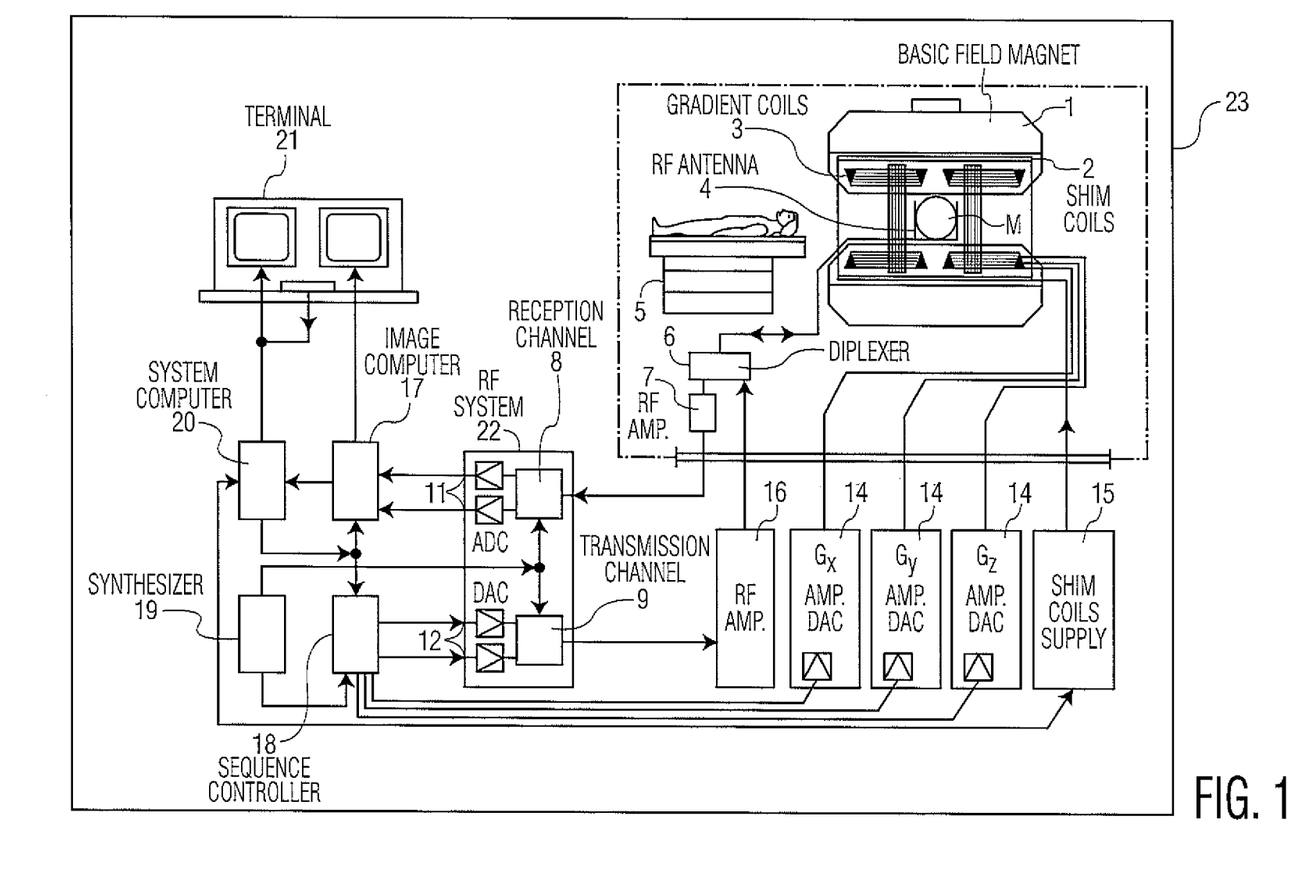
FIG. 1 is a schematic block diagram of a magnetic resonance imaging system, according to invention principles.

FIG. 1 is a schematic block diagram of a system 23 including a magnetic resonance tomography device with which MR weighted images can be acquired according to principles of the present invention. A basic field magnet 1 generates a strong magnetic field, which is constant in time, for the polarization or alignment of the nuclear spins in the examination region of an object, such as, for example, a part of a human body to be examined. The high homogeneity of the basic magnetic field required for the magnetic resonance measurement is provided in a spherical measurement volume M, for example, into which the parts of the human body to be examined are brought. In order to satisfy the homogeneity requirements and especially for the elimination of time-invariant influences, shim-plates made of ferromagnetic material are mounted at suitable positions. Time-variable influences are eliminated by shim coils 2, which are controlled by a shim-current supply 15.

In the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence control 18 for the generation of gradient pulses at proper times.

Within the gradient field system 3, a radio-frequency antenna 4 is located which converts the radio-frequency pulses emitted by a radio-frequency power amplifier 16 via multiplexer 6 into a magnetic alternating field in order to excite the nuclei and align the nuclear spins of the object to be examined or the region of the object to be examined. From the radio-frequency antenna 4, the alternating field emerging from the precessing nuclear spins, i.e. usually the nuclear spin echo signals brought about by a pulse sequence from one or more high-frequency pulses and one or more gradient pulses, is converted into a voltage that is supplied via an amplifier 7 and multiplexer 6 to a radio-frequency receiver channel 8 of a radio-frequency system 22. The radio-frequency system 22 contains, a transmission channel 9, conveying radio-frequency pulses representing the nuclear magnetic resonance. In the process, the respective radio-frequency pulses based on a pulse sequence specified by the system computer 20 in the sequence control 18 are represented digitally as complex numbers. This numerical sequence is supplied as real and imaginary parts via inputs 12 to a digital-analog converter in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M.

The conversion from transmitting to receiving operation is done via a multiplexer 6. The radio-frequency antenna 4 emits the radio-frequency pulse to excite the nuclear spin in the measurement volume M and scans the resultant echo signals. The correspondingly obtained magnetic resonance signals are demodulated in the receiving channel 18 of the radio-frequency system 22 in a phase-sensitive manner, and are converted via respective analog-digital converter into a real part and an imaginary part of the measurement signal. Using an imaging computer 17, an image is reconstructed from the measurement data obtained in this way. The administration of the measurement data, the image data and the control programs is done via the system computer 20. Based on a specification with control programs, the sequence control 18 controls the generation of the desired pulse sequences and the corresponding scanning of k-space. In particular, the sequence control 18 controls the switching of the gradients at appropriate times, the transmission of the radio-frequency pulses with a defined phase and amplitude, and the reception of the magnetic resonance signals. The time basis for the radio-frequency system 22 and the sequence control 18 is furnished by a synthesizer 19. The selection of appropriate control programs for generating an MR image and the display of the generated nuclear spin image is done via a terminal (console) 21, which contains a keyboard and one or more screens.

System computer 20 automatically (or in response to user command entered via terminal 21) employs and directs the MR imaging device to acquire first, second, third and fourth images. Specifically, in the absence of a contrast agent, in a patient anatomical volume of interest including lymph nodes, the MR imaging device acquires a first image optimized for Lymph node enhancement, using a breath hold 3D SPACE compatible acquisition process, for example. The MR imaging device acquires the second image using a breath hold 3D Susceptibility Weighted Imaging (SWI) compatible acquisition process and acquires a third image using a breath hold 2D Diffusion Weighted Imaging (DWI) compatible acquisition process that emphasizes malignant lymph node regions. The inventors advantageously recognize that optimized 3D DWI sequences in one embodiment obtain results with even further improvement. Further, in the presence of a contrast agent (e.g., an Ultra small Super Paramagnetic Iron Oxide nano-particle (USPIO) compatible agent) absorbed by benign lymph nodes, in the patient anatomical volume of interest, the MR imaging device acquires a fourth image using a breath hold 3D Susceptibility Weighted Imaging (SWI) compatible acquisition process. System computer 20 processes data representing the first, second, third and fourth images for display on a reproduction device (e.g., terminal 21) and substantially adjacent enabling user comparison of images.

A user interface of terminal 21 (e.g., mouse, keyboard, touchscreen, voice processor, not shown to preserve drawing clarity) enables a user to visualize lymph nodes in at least one of the first, second, third and fourth images presented on terminal 21. It is recognized the nodes are likely to be best identified on SPACE images since the human eye perceives bright objects better than dark ones. System computer 20 processes data associated with the lymph nodes. Specifically, System computer 20 processes image representative datasets to align images by employing a rigid or a non-rigid registration process for processing acquired image representative datasets to align the second, third and fourth images with the first images. The rigid registration method uses maximization of mutual information between the two datasets. The non-rigid registration addresses motion compensation problems in dynamic lung studies. The dense transformation between the images may be modeled as a mapping in the image domain. It is obtained by computing iteratively the steady state of an evolution equation of the form $\partial\Phi/\partial t = D\Phi \cdot v$, $\Phi(0)$ =identity, where v is a regularized velocity field induced by a local statistical similarity measure. In the context of LNP enhanced data, the use of local statistics particularly are effective to discriminate between the contrast agent intake and misalignment. To improve both the speed and the capture range of the method, the system is implemented in combination with a multi-resolution method in which initial estimates of the deformation are obtained from coarse representations of the images and later refined at higher resolutions.

The first images serve as the reference set where Lymph nodes are bright whether malignant or benign. System computer 20 substantially subtracts data representing image content of the second image from the fourth image to provide image difference content that when superimposed on SPACE images provides representative data of an image emphasizing benign lymph node regions. This process eliminates the benign lymph nodes from the list of lymph nodes highlighted by the SPACE images. System computer 20 further processes image representative data to superimpose the third image on the SPACE images to provide an image facilitating identification of malignant lymph nodes. This process not only identifies malignant and benign lymph nodes, but also substantially eliminates artifacts that may mimic lymph nodes on an individual dataset from amongst the 4 sets of images.

Figure 2:
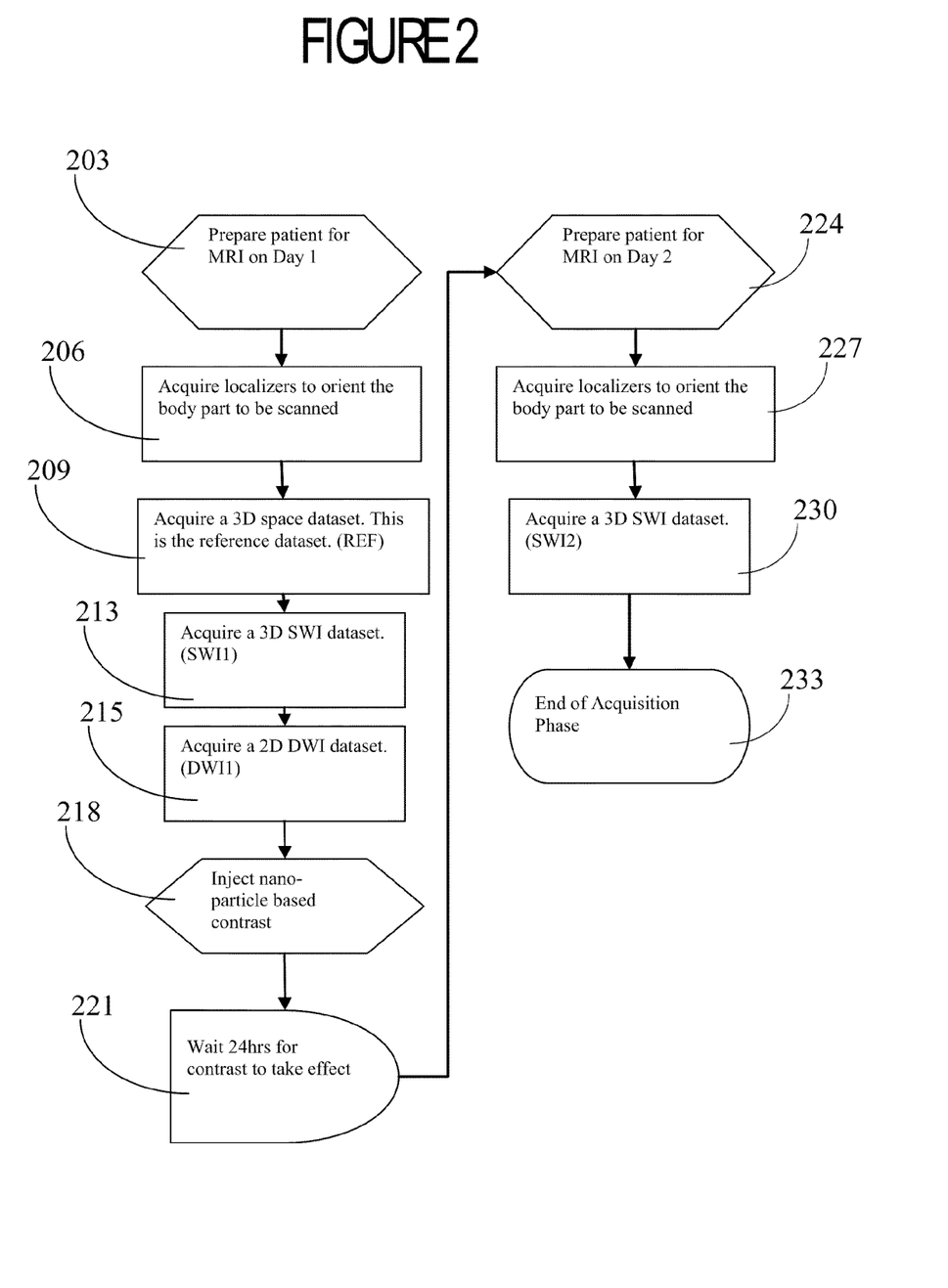
FIG. 2 shows a flowchart of a process performed by a system for image data acquisition and detection of malignant lymph nodes using an MR imaging device, according to invention principles.
Figure 4:
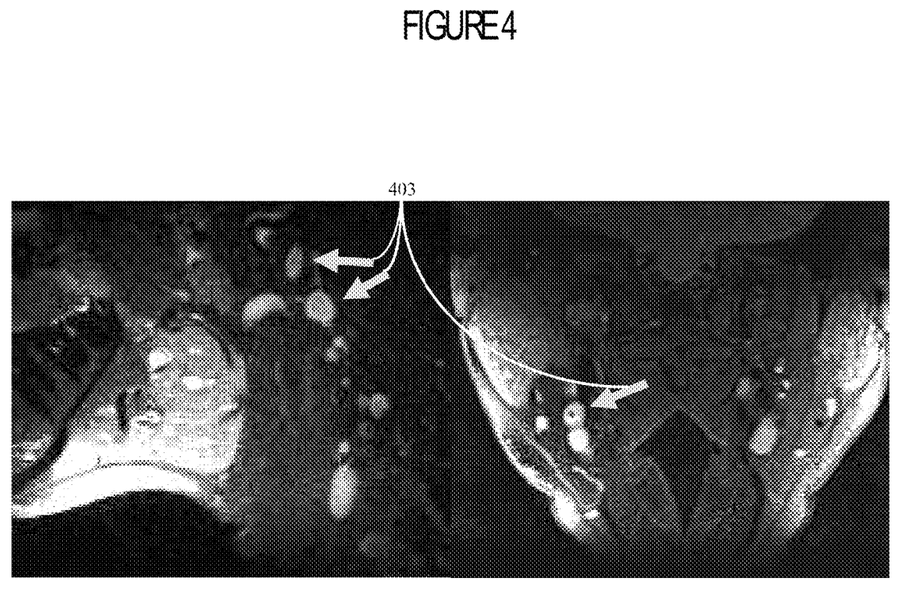
FIG. 4 illustrates a lymph node high resolution isotropic 3D SPACE image dataset acquired by a system for detecting malignant lymph nodes using an MR imaging device, according to invention principles.

FIG. 2 shows a flowchart of a process performed by a system for image data acquisition and detection of malignant lymph nodes using an MR imaging device in system 23 (FIG. 1). In step 203 a patient is prepared for MRI on day 1. In step 206, System computer 20 initiates performance of a localizer MR imaging sequence to orient a patient anatomical volume of interest to be scanned. In the absence of a contrast agent, in step 209, System computer 20 initiates acquisition by the MR device of a first image comprising a reference dataset (REF) using a variable flip angle, lymph node enhancing, MR image acquisition process in a patient anatomical volume of interest, including lymph nodes. In one embodiment, this acquisition process comprises a breath hold 3D SPACE (or equivalent) acquisition that is targeted to enhance the appearance of Lymph nodes and is acquired over the volume of interest to visualize lymph nodes. One millimeter isotropic (identical in all directions) acquisition ensures that no nodes are missed in the volume of interest. If required, several volumes are acquired to compensate for respiratory motion. In this acquisition the lymph nodes have sufficiently high contrast that enables good segmentation and localization. FIG. 4 illustrates a first image acquired by system 23 using a breath hold 3D SPACE acquisition comprising an enhanced lymph node 3D image dataset and presented on display 21. Arrows 403 identify lymph nodes.

Figure 5:
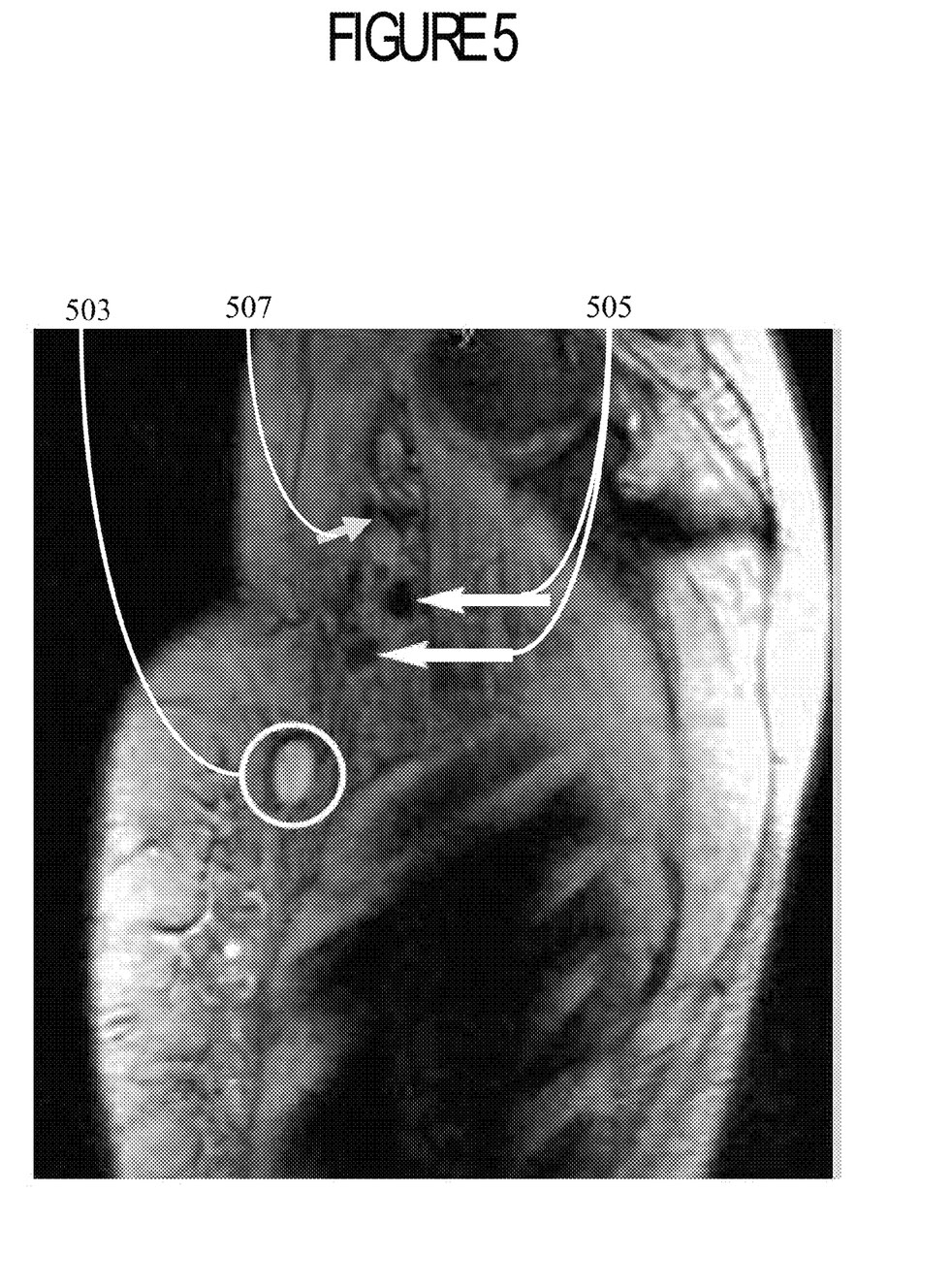
FIG. 5 illustrates a susceptibility weighted lymph node view of a 3D image acquired by a system for detecting malignant lymph nodes using an MR imaging device, according to invention principles.

In the absence of a contrast agent, in step 213, System computer 20 initiates acquisition by the system 23 MR device of a second image dataset comprising a 3D dataset using a susceptibility weighting imaging acquisition process. Specifically, the system 23 MR device in one embodiment acquires a breath hold 3D susceptibility weighted dataset over the same volume of interest to visualize lymph nodes. Use of a one millimeter isotropic acquisition ensures that nodes are not missed in the volume of interest. Further, multiple 3D datasets of the volume of interest are acquired to compensate for respiratory motion, if required. This acquisition acts as a surrogate for the previous acquisition of step 209 and facilitates identification of pre and post contrast malignant lymph nodes, specifically post contrast images. FIG. 5 illustrates a susceptibility weighted lymph node image acquired by the system 23 MR device. A malignant node is identified by circle 503 and benign (dark) nodes are identified by arrows 505. Dark nodes such as the node identified by arrow 507 that blend with other similar structures in the background are the ones that are usually missed.

Figure 6:
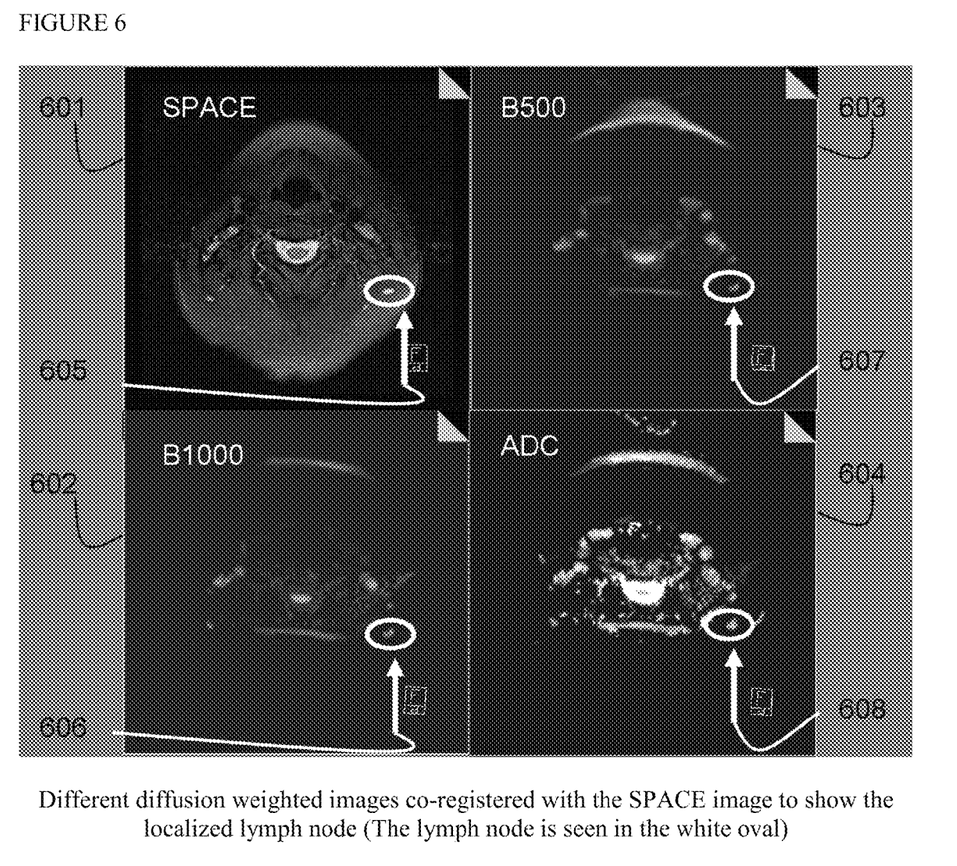
FIG. 6 illustrates different diffusion weighted lymph node 2D images (B, C and D) in comparison with SPACE image 2D image (A) acquired by a system for detecting malignant lymph nodes using an MR imaging device, according to invention principles.

In step 215 System computer 20 initiates acquisition by the MR device of a third image 2D dataset using a diffusion weighting imaging acquisition process, in the absence of a contrast agent. Specifically, the system 23 MR device in one embodiment acquires a 2D diffusion weighted dataset to cover lymph nodes as it is difficult or impossible to acquire a high resolution isotropic dataset within reasonable time limits. Malignant lymph nodes are clearly visible using diffusion imaging as bright spots as these regions have low diffusion. FIG. 6 illustrates different diffusion weighted lymph node 2D images acquired by system. Image 601 is a SPACE image. Images 602 and 603 are a diffusion weighted images with different diffusion weight (b-value) and 604 is an apparent diffusion coefficient map (DWI-ADC). The lymph node is identified by arrows 605, 606, 607 and 608 respectively. Specifically, the lymph node is shown by arrow 608 in the DWI-ADC map as being relatively bright.

In step 218, a nano-particle (LNP) based contrast agent is introduced to the patient volume of interest to be scanned and in step 224 the patient is prepared for MRI on day 2 following day 1 after a 24 hour wait in step 221 following the introduction of the contrast agent. In step 227, System computer 20 initiates performance of a localizer MR imaging sequence to orient the patient anatomical volume of interest to be scanned. In step 230 in the presence of the introduced nano-particle contrast agent absorbed by benign lymph nodes, System computer 20 initiates acquisition by the MR device of a fourth image using a susceptibility weighting imaging acquisition process in the patient anatomical volume of interest. The image acquisition phase ends in step 233.

Figure 3:
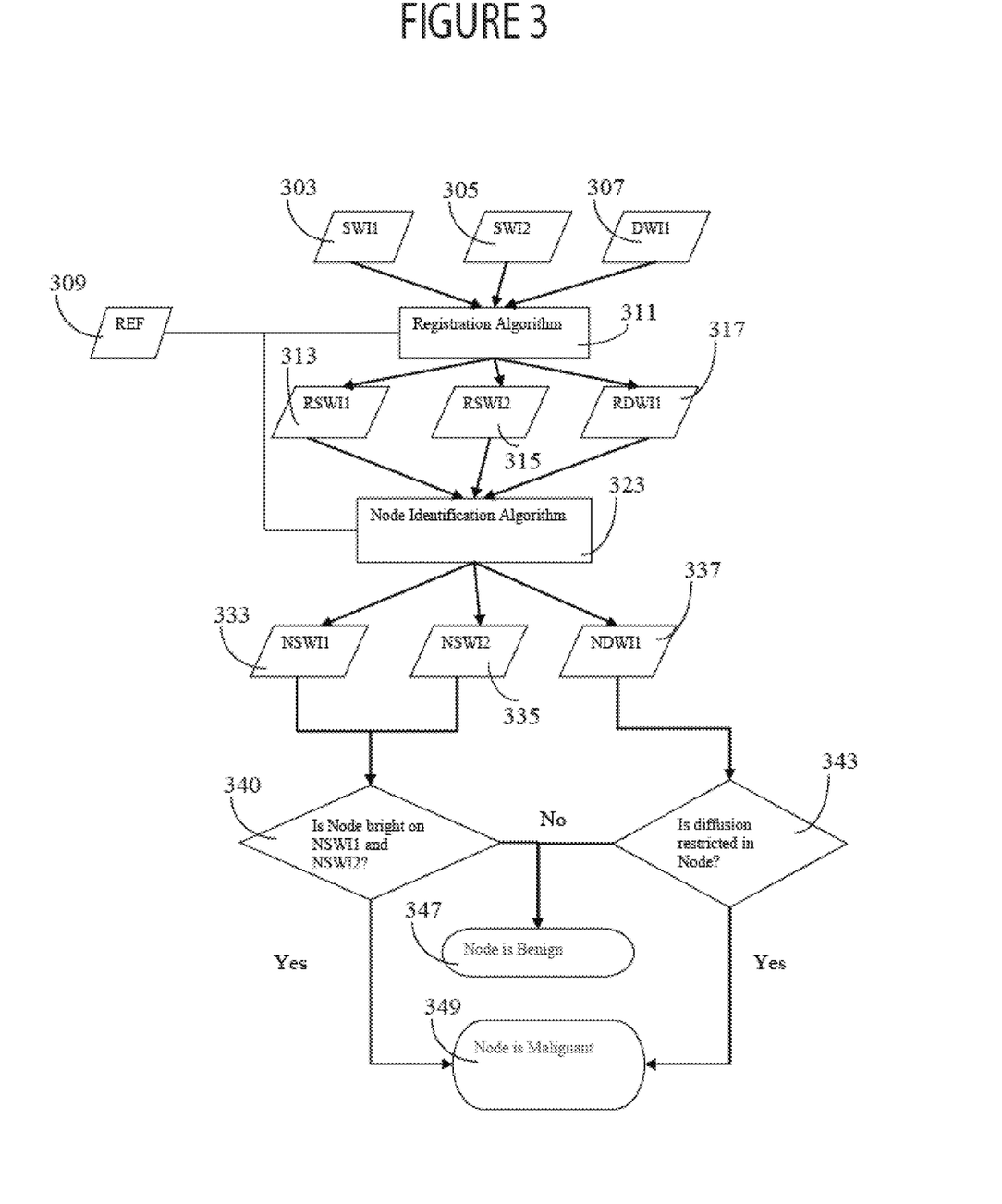
FIG. 3 shows a flowchart of acquired image data post-processing performed by a system for detecting malignant lymph nodes using an MR imaging device, according to invention principles.

FIG. 3 shows a flowchart of acquired image data post-processing performed by system computer 20. System computer 20 in step 311 co-registers acquired MR images comprising image datasets acquired prior to and following introduction of the LNP contrast agent. Specifically, System computer 20 co-registers (aligns) pre-contrast agent susceptibility weighted image dataset (SWI1) 303, pre-contrast agent diffusion weighted image dataset, including Apparent Diffusion Coefficient Maps (DWI1) 307 and post-contrast agent susceptibility weighted image dataset (SWI2) 305 whilst keeping breath hold 3D SPACE dataset (REF) 309 (e.g. acquired using T2 weighted 3D variable flip angle, Lymph node enhancing, Turbo (Fast) Spin Echo dataset) as reference. System computer 20 mutually aligns datasets (SWI1) 303, (SWI2) 305 and (DWI1) 307 in a rigid or non-rigid manner keeping REF dataset 309 as a reference, by using one of a number of known image alignment processes such as using edge detection by thresholding luminance data transitions and determining linear translation shifts in multiple axes. Thereby System computer 20 provides image datasets (RSW1) 313, (RSWI2) 315 and (RDWI1) 317 comprising registered (mutually aligned) image datasets corresponding to datasets (SWI1) 303, (SWI2) 305 and (DWI1) 307, respectively and aligned with respect to REF image dataset 309.

System computer 20 in step 323 subtracts aligned datasets 313 and 315 comprising pre-contrast agent susceptibility weighted image 313 and post-contrast agent susceptibility weighted image 315 respectively, to provide a ΔSWI image dataset showing probable benign regions. Pre-contrast agent diffusion weighted image dataset (RDWI1) 317 identifies probable malignant regions. System computer 20 identifies lymph nodes automatically (or semi-automatically in another embodiment) in the SPACE image (REF) dataset 309 to facilitate automatic identification by system computer 20 of corresponding nodes in the ΔSWI image dataset and diffusion weighted image dataset (RDWI1) 317. Nodes are identified by using one of a number of known node identification processes such as prior shape and size information. System computer 20 generates image datasets (NSWI1) 333, (NSWI2) 335 and (NDWI1) 337 comprising nodes extracted from corresponding image datasets (RSW1) 313, (RSWI2) 315 and (RDWI1) 317 respectively, with respect to nodes from (REF) dataset 309.

The process of labeling nodes as malignant or benign is simplified by the identification by System computer 20 of the lymph nodes in the ΔSWI and (RDWI1) 317 image datasets. The information in the ΔSWI image dataset showing probable benign regions supplemented by information in image dataset (RDWI1) 317 identifying probable malignant regions, facilitates identification by System computer 20 of malignant nodes and adds robustness to the process. System computer 20 in step 340 automatically identifies whether individual lymph nodes in image datasets (NSWI1) 333 and (NSWI2) 335 are bright by determining whether node luminance values exceed a predetermined threshold. If a node in an image is classified as bright in step 340, System computer 20 identifies it as malignant by a visual indicator in the image in step 349. Otherwise the node is classified as benign in step 347. System computer 20 in step 343 automatically identifies whether water molecule diffusion is restricted in individual lymph nodes in image dataset (NDWI1) 337 by determining whether the diffusion exceeds a predetermined threshold (ADC value) with respect to historically predetermined diffusion values. If a node in an image is classified as restricted in step 343, System computer 20 identifies it as malignant by a visual indicator in the image in step 349. Otherwise the node is classified as benign in step 347.

Figure 7:
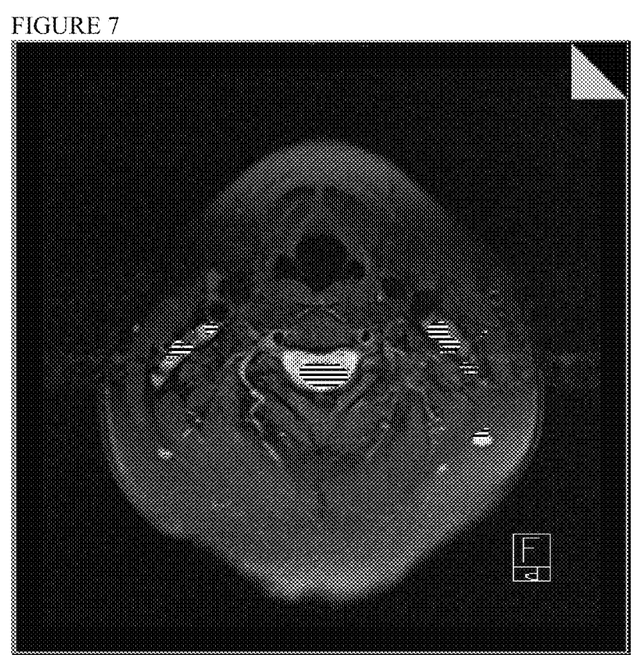
FIG. 7 illustrates a grayscale SPACE image overlaid with combined regions of mutual interest from diffusion weighted lymph node 2D image as represented by hatched regions provided by a system for detecting malignant lymph nodes using an MR imaging device, according to invention principles.

System computer 20 processes the ΔSWI, (RDWI1) 317 and (REF) 309 image datasets through fusing (REF) 309 image data with DWI and ΔSWI data by overlaying the images on each other with different color scales to depict areas of mutual concurrence or lack of it. Resultant fused image data superimposes probable malignant and benign lymph nodes over readily identifiable lymph nodes thereby eliminating regions that do not belong to lymph nodes and increasing accuracy of detecting malignant lymph nodes. System computer 20 in conjunction with processor 34 processes the fused image data and ΔSWI, (RDWI1) 317 and (REF) 309 image datasets for presentation on display 21. FIG. 7 illustrates a grayscale representation of a grayscale (REF) 309 image fused with a diffusion weighted lymph node 2D image (RDWI1) 317 highlighting potential lymph node regions. The FIG. 7 image is presented in grayscale but represents a color scale image, the color regions replaced with hatched regions.

Figure 8:
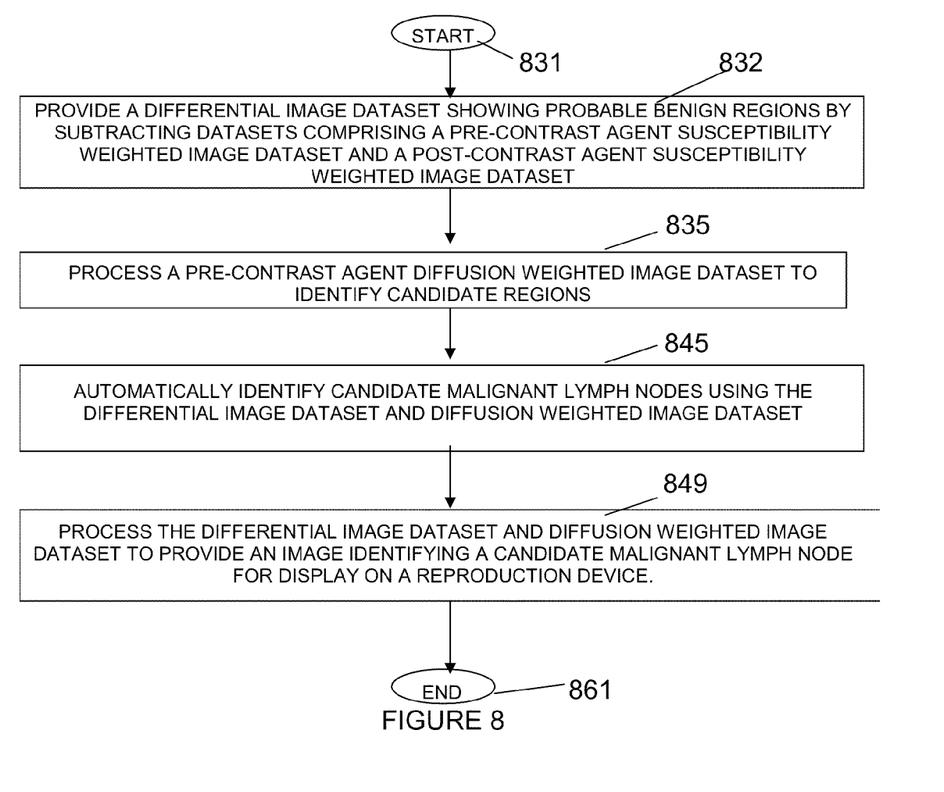
FIG. 8 shows a flowchart of a process performed by a system for detection of malignant lymph nodes using an MR imaging device, according to invention principles.

FIG. 8 shows a flowchart of a process performed by system 23 for detection of malignant lymph nodes using an MR imaging device. In step 832 following the start at step 831, System computer 20 provides a differential image dataset showing probable benign regions by subtracting datasets comprising a pre-contrast agent (e.g., a USPIO compatible agent) susceptibility weighted image dataset and a post-contrast agent susceptibility weighted image dataset. In step 835, System computer 20 processes a pre-contrast agent diffusion weighted image dataset to identify candidate malignant regions. System computer 20 processes the pre-contrast agent susceptibility weighted image dataset, the post-contrast agent susceptibility weighted image dataset, the pre-contrast agent diffusion weighted image dataset and an image dataset acquired using a variable flip angle, lymph node enhancing MR image acquisition process (e.g., SPACE), to identify lymph nodes. In step 845 automatically identifies candidate benign lymph nodes using the differential image dataset and malignant lymph nodes using diffusion weighted image dataset.

System computer 20 identifies malignant lymph nodes in the pre-contrast agent susceptibility weighted image dataset and the post-contrast agent susceptibility weighted image dataset in response to detected node luminance exceeding a predetermined threshold. System computer 20 automatically identifies malignant lymph nodes in the diffusion weighted image dataset in response to restricted diffusion in a node detected by analysis of luminance (ADC) within the area of the node. In step 849, System computer 20 (with display processor 21) processes the differential image dataset and diffusion weighted image dataset to provide an image identifying a candidate malignant lymph node with a visual indicator in an image for display on a reproduction device (e.g., terminal 21). The process of FIG. 8 terminates at step 861.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system comprises an MR imaging device using corresponding different pulse sequences to acquire and process different types of image to enhance and automatically identify malignant lymph nodes using a USPIO contrast agent, for example, for display on a reproduction device. Further, the processes and applications may, in alternative embodiments, be located on one or more (e.g., distributed) processing devices on the network of FIG. 1. Any of the functions and steps provided in FIGS. 1-8 may be implemented in hardware, software or a combination of both.

What is claimed is:

1. A system for detecting malignant lymph nodes using an MR imaging device, comprising:
    an MR imaging device configured in response to predetermined instructions for,
        in the absence of a contrast agent, acquiring in a patient anatomical volume of interest including lymph nodes,
            (a) a first image using a variable flip angle, lymph node enhancing, MR image acquisition process,
            (b) a second image using a susceptibility weighting imaging acquisition process and
            (c) a third image using a diffusion weighting imaging acquisition process for identifying malignant lymph nodes and
        in the presence of a contrast agent absorbed by benign lymph nodes, acquiring in said patient anatomical volume of interest,
            (d) a fourth image using a susceptibility weighting imaging acquisition process; and
    a display processor for processing data representing the first, second, third and fourth images to provide images facilitating identification of malignant and benign lymph nodes for display on a reproduction device.

2. A system according to claim 1, wherein
    said display processor processes data representing the first, second, third and fourth images for adjacent display enabling user comparison of images.

3. A system according to claim 1, including
    a user interface enabling a user to select particular lymph nodes in at least one of the first, second, third and fourth images displayed on said reproduction device and
    an image data processor for processing data associated with the selected lymph nodes.

4. A system according to claim 1, including
    an image data processor for processing image representative datasets to align the second, third and fourth image with the first images.

5. A system according to claim 4, wherein
    said image data processor employs at least one of, (a) a rigid registration process and (b) a non-rigid registration process for processing image representative datasets to align the to align the second, third and fourth image with the first images.

6. A system according to claim 1, including
    an image data processor for substantially subtracting data representing image content of said second image from said fourth image to provide image difference content representative data of an image emphasizing benign lymph node regions.

7. A system according to claim 6, wherein
    said image data processor processes image representative data to superimpose the third image on the reference image data to provide an image facilitating identification of malignant lymph nodes.

8. A system according to claim 1, wherein
    said third image emphasizes malignant lymph node regions.

9. A system according to claim 1, wherein
    said contrast agent is an Ultra small Super Paramagnetic Iron Oxide nano-particle (USPIO) compatible agent.

10. A system according to claim 1, wherein
    said first image is acquired by said MR imaging device using a breath hold 3D SPACE compatible acquisition process.

11. A system according to claim 1, wherein
    said second image is acquired by said MR imaging device using a breath hold 3D Susceptibility Weighted Imaging (SWI) compatible acquisition process.

12. A system according to claim 1, wherein
    said third image is acquired by said MR imaging device using a breath hold 2D Diffusion Weighted Imaging (DWI) compatible acquisition process.

13. A system according to claim 1, wherein
    said fourth image is acquired by said MR imaging device using a breath hold 3D Susceptibility Weighted Imaging (SWI) compatible acquisition process.

14. A system for detecting malignant lymph nodes by processing images acquired using an MR imaging device, comprising:
    an image data processor configured in response to predetermined instructions for,
        providing a differential image dataset showing probable benign regions by subtracting datasets comprising a pre-contrast agent susceptibility weighted image dataset and a post-contrast agent susceptibility weighted image dataset, processing a pre-contrast agent diffusion weighted image dataset to identify candidate regions identifying malignant lymph nodes and automatically identifying candidate malignant lymph nodes using the differential image dataset and diffusion weighted image dataset; and a display processor for processing the differential image dataset and diffusion weighted image dataset to provide an image identifying a candidate malignant lymph node for display on a reproduction device.

15. A system according to claim 14, wherein said image data processor processes at least one of, the pre-contrast agent susceptibility weighted image dataset, the post-contrast agent susceptibility weighted image dataset and the pre-contrast agent diffusion weighted image dataset to identify lymph nodes.

16. A system according to claim 15, wherein said image data processor performs the step of identifying lymph nodes by processing an image dataset acquired using a variable flip angle, lymph node enhancing, MR image acquisition process.

17. A system according to claim 16, wherein said variable flip angle, lymph node enhanced contrast, MR image acquisition process comprises a SPACE (Sampling Perfection with Application optimized Contrast) compatible acquisition.

18. A system according to claim 14, wherein said image data processor identifies benign lymph nodes in the pre-contrast agent susceptibility weighted image dataset and the post-contrast agent susceptibility weighted image dataset in response to detected node luminance.

19. A system according to claim 18, wherein said image data processor automatically identifies malignant lymph nodes in the post-contrast agent susceptibility weighted image dataset in response to detected node luminance exceeding a predetermined threshold.

20. A system according to claim 14, wherein said image data processor automatically identifies malignant lymph nodes in the diffusion weighted image dataset in response to restricted diffusion in a node detected by analysis exceeding a predetermined threshold.

21. A system according to claim 14, wherein said display processor automatically provides an image identifying a lymph node as malignant with a visual indicator.

22. A system according to claim 14, wherein said contrast agent is an Ultra small Super Paramagnetic Iron Oxide nano-particle (USPIO) compatible agent.

23. A method for detecting malignant lymph nodes by processing images acquired using an MR imaging device, comprising the activities of:

employing at least one computer for, providing a differential image dataset showing probable benign regions by subtracting datasets comprising a pre-contrast agent susceptibility weighted image dataset and a post-contrast agent susceptibility weighted image dataset, processing a pre-contrast agent diffusion weighted image dataset to identify candidate regions for identifying malignant lymph nodes and automatically identifying candidate malignant lymph nodes using the differential image dataset and diffusion weighted image dataset; and processing the differential image dataset and diffusion weighted image dataset to provide an image identifying a candidate malignant lymph node for display on a reproduction device.

\* \* \* \* \*